(12) United States Patent
Singh

(10) Patent No.: US 11,772,140 B2
(45) Date of Patent: Oct. 3, 2023

(54) CLEANING DEVICE FOR BLOOD VESSEL SEALING APPARATUS

(71) Applicant: City of Hope, Duarte, CA (US)

(72) Inventor: Gagandeep Singh, Duarte, CA (US)

(73) Assignee: City of Hope, Duarte, CA (US)

( * ) Notice: Subject to any disclaimer, the term of this patent is extended or adjusted under 35 U.S.C. 154(b) by 53 days.

(21) Appl. No.: 17/371,531

(22) Filed: Jul. 9, 2021

(65) Prior Publication Data

US 2021/0331217 A1    Oct. 28, 2021

Related U.S. Application Data

(62) Division of application No. 16/253,945, filed on Jan. 22, 2019, now Pat. No. 11,077,473.

(60) Provisional application No. 62/622,392, filed on Jan. 26, 2018.

(51) Int. Cl.
| | | |
|---|---|---|
| B08B 9/043 | (2006.01) | |
| A46B 3/18 | (2006.01) | |
| A61B 17/00 | (2006.01) | |
| B08B 1/00 | (2006.01) | |
| B08B 1/04 | (2006.01) | |

(52) U.S. Cl.
CPC ........ B08B 9/0436 (2013.01); A61B 17/0057 (2013.01); B08B 1/002 (2013.01); B08B 1/04 (2013.01); *A46B 3/18* (2013.01); *A61B 2017/00637* (2013.01)

(58) Field of Classification Search
CPC .......... B08B 9/043; B08B 9/0436; A46B 3/18
See application file for complete search history.

(56) References Cited

U.S. PATENT DOCUMENTS

| | | | | | |
|---|---|---|---|---|---|
| 4,344,203 | A | * | 8/1982 | Gerrick | .................. A63B 47/04 15/21.2 |
| 4,965,906 | A | * | 10/1990 | Mauro | .................. A63B 57/60 15/21.2 |
| 5,555,586 | A | * | 9/1996 | Dorrich | .................. A63B 47/04 15/21.2 |
| 6,233,774 | B1 | * | 5/2001 | Vogt | ........................ A63B 47/04 15/210.1 |
| 6,745,424 | B1 | * | 6/2004 | Pimentel | ................ A63B 57/60 15/21.2 |
| 2019/0133674 | A1 | | 5/2019 | Singh | |
| 2019/0232343 | A1 | * | 8/2019 | Singh | ........................ B08B 1/04 |

OTHER PUBLICATIONS

IP.com pdf for case U.S. Appl. No. 16/253,945, filed Jan. 22, 2019. 6 pages.

* cited by examiner

*Primary Examiner* — Michael D Jennings
(74) *Attorney, Agent, or Firm* — Mintz Levin Cohn Ferris Glovsky and Popeo, P.C.

(57) ABSTRACT

A cleaner device is adapted to clean a blood vessel sealer device. The cleaner device includes a series of brushes that can move relative to blood vessel sealer device to scrub and clean the blood vessel sealer device when coupled to the cleaner device. The brushes can be made of any material that is adapted to clean the blood vessel sealer device. The cleaner device can also be motorized to facilitate cleaning of the blood vessel sealer device.

10 Claims, 2 Drawing Sheets

CLEANING DEVICE FOR BLOOD VESSEL SEALING APPARATUS

REFERENCE TO PRIORITY DOCUMENT

This application is a divisional of U.S. application Ser. No. 16/253,945 entitled "CLEANING DEVICE FOR BLOOD VESSEL SEALING APPARATUS" filed Jan. 22, 2019 and claims priority to U.S. Provisional Application Ser. No. 62/622,392 entitled "CLEANING DEVICE FOR BLOOD VESSEL SEALING APPARATUS" and filed on Jan. 26, 2018. The contents of which are herein incorporated by reference in their entirety.

BACKGROUND

A blood vessel sealing device or apparatus is a device that is used to seal a blood vessel in order to achieve hemostasis. Such vessel sealing devices accumulate debris during use such that a user must frequently clean such devices during a blood vessel sealing procedure or other procedure. A clinician typically performs this cleaning process by using a separate gauze piece or lap pad on the sealing device. This can be fairly ineffective as the sealing device undergoes repeated use. The user often is required to perform a cleaning process on a regular basis during the sealing procedure, such as at a frequency of every 2 minutes.

This can be a cumbersome and tedious process. It is also dependent on the diligence of the user. This can result in ineffective cleaning of the blood vessel sealing device, which can be harmful for a patient.

In view of the foregoing, there is a need for improved devices and methods for cleaning a blood vessel sealing device.

SUMMARY

Disclosed is a cleaner device that is adapted and configured to clean a blood vessel sealer device or other instrument that requires a cleaning, such as a cleaning of an end portion of a medical interventional device. For example, the cleaner device can be used to clean a forceps, a pick up, or a suction tip. The cleaner device has a simple and elegant mechanical configuration that can work with any of a multitude of blood vessel sealer devices. The cleaner device includes a series of brushes that can move relative to blood vessel sealer device to scrub and clean the blood vessel sealer device when coupled to the cleaner device. The brushes can be made of any material that is adapted to clean the blood vessel sealer device. The cleaner device can also be motorized to facilitate cleaning of the blood vessel sealer device.

In one aspect, there is disclosed a system for cleaning a vessel sealer device, comprising: a housing defining a cavity; and at least one brush inside the cavity, the at least one brush is positioned inside the cavity such that at least a portion of a blood vessel sealer device can be inserted inside the cavity in contact with the at least one brush; wherein the at least one brush can be moved relative to the at least a portion of a blood vessel sealer device so as to scrub the at least a portion of a blood vessel sealer device when the at least a portion of a blood vessel sealer device is inside the cavity.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The details of one or more variations of the subject matter described herein are set forth in the accompanying drawings and the description below. Other features and advantages of the subject matter described herein will be apparent from the description and drawings, and from the claims.

DETAILED DESCRIPTION

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

Disclosed is a cleaner device that is adapted and configured to clean a blood vessel sealer device. The cleaner device has a simple and elegant mechanical configuration that can work with any of a multitude of blood vessel sealer devices. The cleaner device includes a series of brushes that can move relative to blood vessel sealer device to scrub and clean the blood vessel sealer device when coupled to the cleaner device. The brushes can be made of any material that is adapted to clean the blood vessel sealer device. The cleaner device can also be motorized to facilitate cleaning of the blood vessel sealer device. In a non-limiting example, the blood vessel sealer device is configured pursuant to the systems, devices and methods described in U.S. patent application Ser. No. 16/177,904 entitled "ENERGY-ENHANCED, HAND-HELD VASCULAR SEALER", which is incorporated herein by reference in its entirety.

Figure 1:
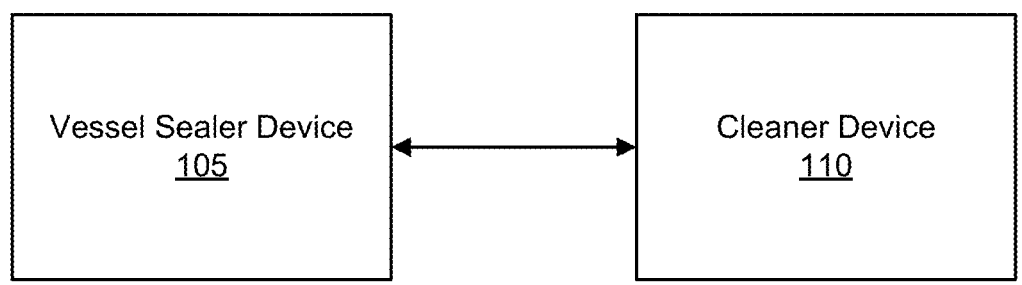
FIG. 1 is a schematic representation of an example blood vessel sealing and cleaning system.

FIG. 1 shows a schematic representation of a blood vessel sealing and cleaning system 100 that includes a vessel sealer device 105 and a cleaner device 110. The cleaner device 110 is adapted and configured to clean the vessel sealer device 105. The cleaner device 110 includes one or more brushes that can be coupled to the vessel sealer device 105, as described below. The brushes are configured to be manually, robotically, and/or automatically moved relative to and in contact with at least a portion of the vessel sealer device 105 to scrub and clean the vessel sealer device 105.

The vessel sealer device can be any type of device that is configured for sealing a blood vessel such as to maintain hemostasis. In a non-limiting example embodiment, the vessel sealer device 105 can be an electro-mechanical, laparoscopic vessel sealing device having a handle and a set of jaws or clamps that are sized and shaped to clamp onto a blood vessel. The device can include one or more electrodes through which an electrical current can be applied to deliver electrical energy to blood vessel tissue for sealing the tissue.

Some examples of vessel sealer devices include the LIGASURE device by Medtronic, Inc., the ENSEAL device by Ethicon-EndoSurgery, the HARMONIC SCALPEL device by Ethicon-EndoSurgery, and the THUNDERBEAT device by Olympus America.

Figure 2:
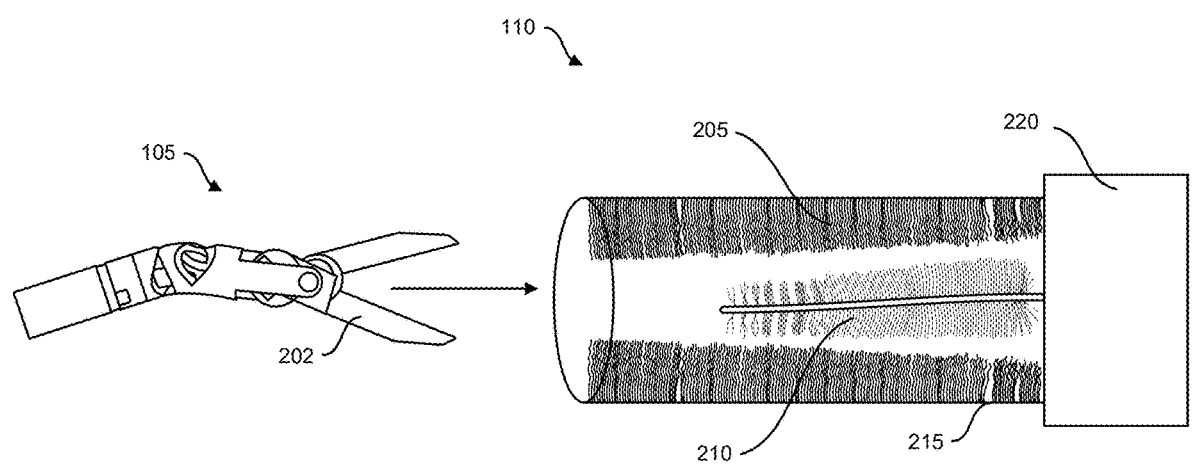
FIG. 2 shows a vessel sealer device and a cleaner device of the system.

FIG. 2 shows a vessel sealer device 105, which includes a pair of electromechanical jaws 202 that can be inserted into or otherwise mechanically coupled to the cleaner device 110. (It should be appreciated that FIG. 2 is not to scale.) The cleaner device 110 includes a set of brushes or bristles including a set of outside brushes 205 that are arranged in an annular formation. That is, the brushes collectively form a tube-shaped opening that is sized and shaped to receive therein at least a portion of the cleaner device 110.

The set of brushes further includes an internal brush 210 positioned within the tube-shaped opening and surrounded by the outside brushes 205. The brushes 205, 210 are positioned inside a tubular housing 215 that is coupled to a hub 220. The housing 215 can be cylindrical such that it defines an internal cavity sized to receive at least a portion of the vessel sealer device 105 including the jaws. The internal cavity also contains the brushes such that, when the vessel sealer device 105 is inserted into the internal cavity, the external or outside brushes 205 can be positioned around the vessel sealer device 105 in an annular relationship. The internal brush 210 can also be positioned inside, between or immediately adjacent the jaws of the vessel sealer device 105. The brushes can be made of any material, such for example a fine metal bristle or a fortified plastic bristle. The material of the brushes is sufficiently hard, rigid, or grainy such that the brushes can wipe off material from the cleaner device when rubbed against the cleaner device.

With reference still to FIG. 2, the hub 220 of the vessel sealer device 105 can include a motor that can cause the housing and/or the brushes to rotate and/or translate relative to the vessel sealer device 105 to achieve a scrubbing or cleaning action of the brushes relative to the vessel sealer device 105. The motor can be an AC or a DC motor and a corresponding power supply can also be included. As an alternative, a use can also manually rotate or otherwise move the cleaner device 110 to achieve such scrubbing or cleaning action. In this regard, the hub 220, a portion of the hub 220, or an internal portion of the hub 220 can rotate relative to the tubular housing 215.

In an embodiment, the hub or some other portion of the cleaner device 110 includes or is coupled to one or more reservoirs that contain a substance such as water, soap etc., wherein such substance can be applied to the vessel sealer device 105 during a cleaning process. At least a portion of the cleaner device 110 can be malleable to permit a user to squeeze the device to cause a pressure differential relative to the reservoir that causes fluid from the reservoir(s) to flow into the internal cavity and in contact with the vessel sealer device 105 during the cleaning process.

In use, a user inserts at least a portion of the vessel sealer device 105 into the cavity of the cleaner device 110 such that at least the jaws or some other portion of the vessel sealer device 105 are in contact with at least some of the brushes of the cleaner device 110. The user then causes the brushes to scrub the vessel sealer device 105 such as by manually moving the brushes or by activating a motor that causes the brushes to move relative to the vessel sealer device 105 and thereby clean the vessel sealer device 105. As mentioned, the external brushes 205 can clean an outside region of the vessel sealer device 105 while the internal brushes can clean an inside region of the vessel sealer device 105.

Upon the brushes scrubbing and/or cleaning the vessel sealer device 105 to a desired or requisite level, the user can remove the vessel sealer device 105 from the cleaner device 110. The user can then continue with use of the vessel sealer device 105.

While this specification contains many specifics, these should not be construed as limitations on the scope of an invention that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. A system for cleaning a blood vessel sealer device, comprising:
   a housing defining a cavity;
   at least one brush inside the cavity, wherein the at least one brush is positioned inside the cavity such that at least a portion of a blood vessel sealer device can be inserted inside the cavity in contact with the at least one brush;
   wherein, when the blood vessel sealer device is at least partially positioned inside the cavity, the at least one brush moves relative to the at least a portion of the blood vessel sealer device so as to scrub the at least a portion of the blood vessel sealer device when the at least a portion of the blood vessel sealer device is inside the cavity; and
   the blood vessel sealer device.

2. The system of claim 1, wherein the at least one brush includes an outer brush and an inner brush.

3. The system of claim 2, wherein the outer brush is positioned to clean an outer portion of the at least a portion of the blood vessel sealer device.

4. The system of claim 2, wherein the inner brush is positioned to clean an inner portion of the at least a portion of the blood vessel sealer device.

5. The system of claim 1, wherein the at least a portion of a blood vessel sealer device is a pair of jaws of the blood vessel sealer device.

6. The system of claim 1, further comprising a motor that moves the at least one brush.

7. The system of claim 1, wherein the at least one brush rotates relative to the housing.

8. The system of claim 1, further comprising a reservoir.

9. The system of claim 8, wherein the reservoir is inside the hub.

10. The system of claim 1, further comprising the vessel sealer device.

* * * * *